US00PP19771P2

(12) United States Plant Patent
Anderson

(10) Patent No.: US PP19,771 P2
(45) Date of Patent: Feb. 24, 2009

(54) ***CHRYSANTHEMUM* PLANT NAMED '00-100-216'**

(50) Latin Name: *Chrysanthemum×hybrida*
Varietal Denomination: 00-100-216

(75) Inventor: Neil O. Anderson, St. Paul, MN (US)

(73) Assignee: Regents of the University of Minnesota, St. Paul, MN (US)

( * ) Notice: Subject to any disclaimer, the term of this patent is extended or adjusted under 35 U.S.C. 154(b) by 0 days.

(21) Appl. No.: 12/006,655

(22) Filed: Jan. 4, 2008

(51) Int. Cl.
*A01H 5/00* (2006.01)

(52) U.S. Cl. ..... Plt./286
(58) Field of Classification Search ..... Plt./286
See application file for complete search history.

(56) References Cited

PUBLICATIONS

Brummit, R. K. "The Garden" "*Chrysanthemum* once again," Sep. 1997, pp. 662–663 (2 pages total).*

* cited by examiner

*Primary Examiner*—Annette H Para
*Assistant Examiner*—S. B. McCormick Ewoldt
(74) *Attorney, Agent, or Firm*—Penny J. Aguirre

(57) ABSTRACT

A new cultivar of *chrysanthemum*, '00-100-216', characterized by it's early blooming habit with frost tolerant single daisy-type inflorescences with maroon red ray florets and gold disk florets, its vigorous shrub-like growth habit after two years of growth, its tight cushion plant form attained without pinching, and its good garden performance and winter hardiness.

2 Drawing Sheets

STATEMENT REGARDING FEDERALLY SPONSORED RESEARCH

This invention was made with government support under MIN-21-50 and MIN-21-52 awarded by the U.S. Dept. of Agriculture. The government has certain rights in the invention.

Botanical classification: *Chrysanthemum×hybrida.*

Variety denomination: '00-100-216'.

BACKGROUND OF THE INVENTION

The present invention relates to a new and distinct cultivar of garden *chrysanthemum* plant, botanically known as *Chrysanthemum×hybrida* '00-100-216' and will be referred to hereinafter by its cultivar name, '00-100-216'. The new cultivar is commercially known as a garden-type *chrysanthemum.*

'00-100-216' was derived from an on going controlled breeding program that focuses on obtaining new cultivars of garden *chrysanthemums* in a range of flower colors that exhibit superior winter hardiness for northern climates, a large shrub-like habit in successive growth years that, and a tight cushion plant habit without the need for pruning or pinching. The breeding originally commenced with crosses utilizing *Dendranthema weyrichii* 'Pink Bomb' (not patented) and various unpatented cultivars of *Dendranthema×grandiflora.*

The new cultivar, '00-100-216', was created with a series of crosses and selections made over a period of years between 1986 and 2000 utilizing proprietary selections. '00-100-216' ultimately originated from a cross-pollination made in 2000 of proprietary seedling designated as '89-98-13' (not patented) as the female parent and the proprietary seedling designated as '00-100-352' (not patented) as the male parent. The new *chrysanthemum* was selected as a single plant within the progeny of the stated cross in 2000 by the inventor in St. Paul, Minn. '00-100-216' was selected as unique for its single, daisy-type inflorescences with maroon red ray florets and gold disk florets combined with the characteristics that fit the objectives of the breeding program.

Asexual reproduction of the new cultivar was first accomplished via stem cuttings in St. Paul, Minn. in 2001. The characteristics of this cultivar have been determined to be stable and are reproduced true to type in successive generations.

SUMMARY OF THE INVENTION

The following traits have been repeatedly observed and are determined to be the characteristics of the new cultivar of *chrysanthemum*. These attributes in combination distinguish '00-100-216' as unique from and all other varieties of *chrysanthemum* known to the inventor.

1. '00-100-216' is early blooming and exhibits single daisy-type inflorescences with maroon red ray florets and gold disk florets.
2. '00-100-216' attains a large shrub-like habit in the second and successive years of growth attaining about 37.5 cm in height and 53 cm in width in the first year and about 44 cm in height and 89 cm in width in the second year.
3. '00-100-216' forms a tight cushion plant form without the need for pinching or pruning.
4. '00-100-216' exhibits extreme hybrid vigor.
5. '00-100-216' exhibits a massive floral display in its second and subsequent years after planting.
6. '00-100-216' is a winter hardy shrub *chrysanthemum* with hardiness to U.S.D.A. Zone 3.
7. The inflorescences of '00-100-216' are frost tolerant.

In comparison to the parent plants; the female parent, '89-98-13', differs from '00-100-216' in having yellow colored flowers, semi-double type flowers, and in having an upright plant habit and the male parent, '00-100-352', differs from '01-127-1' in having yellow colored, triplex daisy type flowers.

'00-100-216' can be compared to 'Empire Salsa' (U.S. Plant Pat. No. 9,578) for its inflorescence form and color, however '00-100-216' exhibits a more uniform cushion plant habit (hemispherical shape), a larger plant size, greater winter hardiness and a massive floral display in its second and subsequent years after planting. '00-100-216' can also be compared to other cultivars originating from the same breeding program with the common characteristics of cold hardiness and having a tight cushion form that becomes shrub-like in second and subsequent growing years; '00-100-382' (U.S. Plant application Ser. No. 11803912)* exhibits single daisy-type inflorescences with dark purple ray florets and '01-127-1' (U.S. Plant patent application Ser. No. 11803967)* exhibits single daisy-type inflorescences with light lavender ray florets. *Examiner has permission to update patent status and replace application Nos with patent numbers if applicable.

BRIEF DESCRIPTION OF THE DRAWINGS

The accompanying colored photographs illustrate the overall appearance and distinct characteristics of the new *chrysanthemum*. The photographs were taken of plants grown for one year under field conditions in Waseca, Minn.

Figure 1:
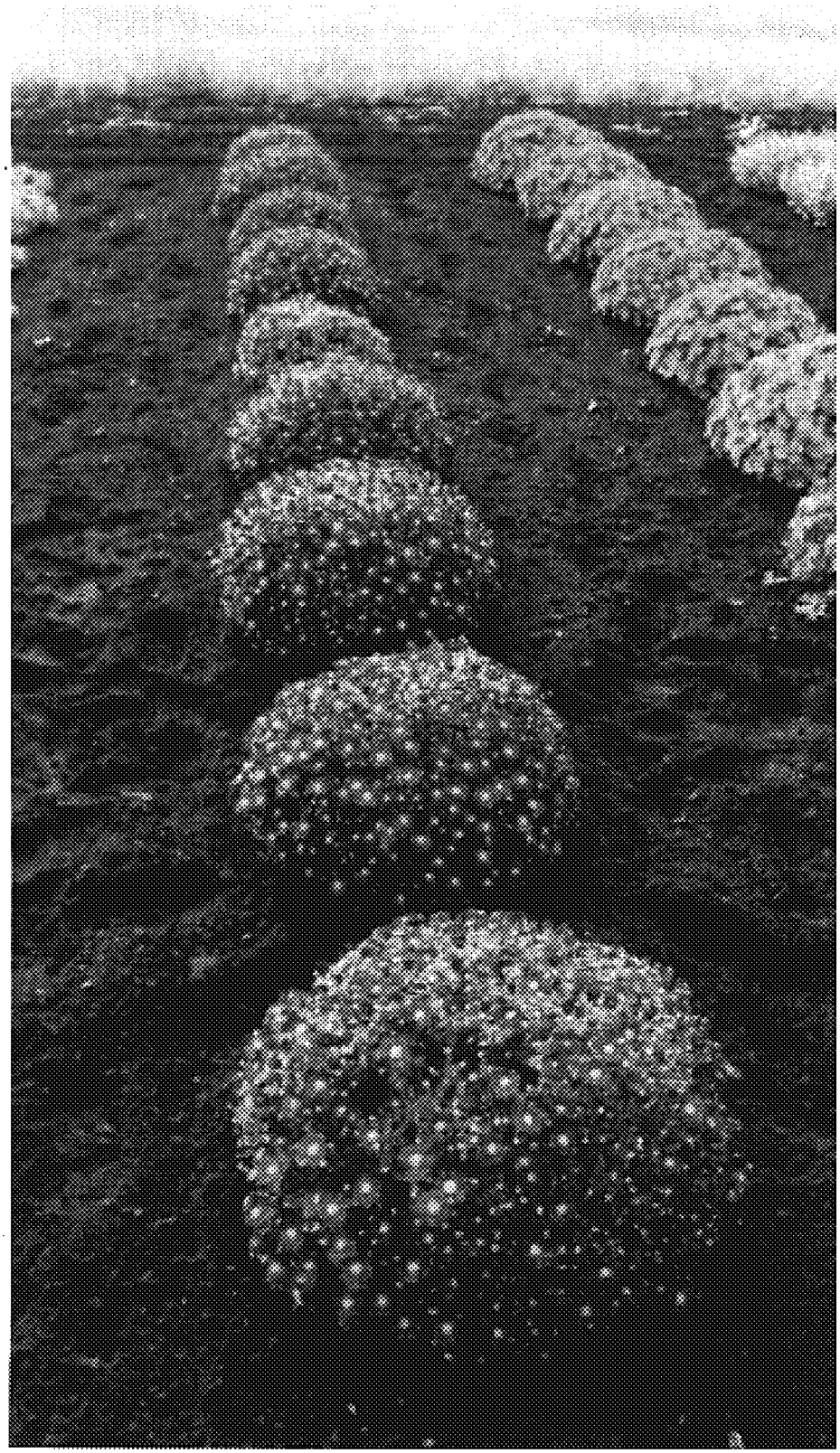
FIG. 1 is a photograph of a row of '00-100-216' plants after one year of growth.
Figure 2:
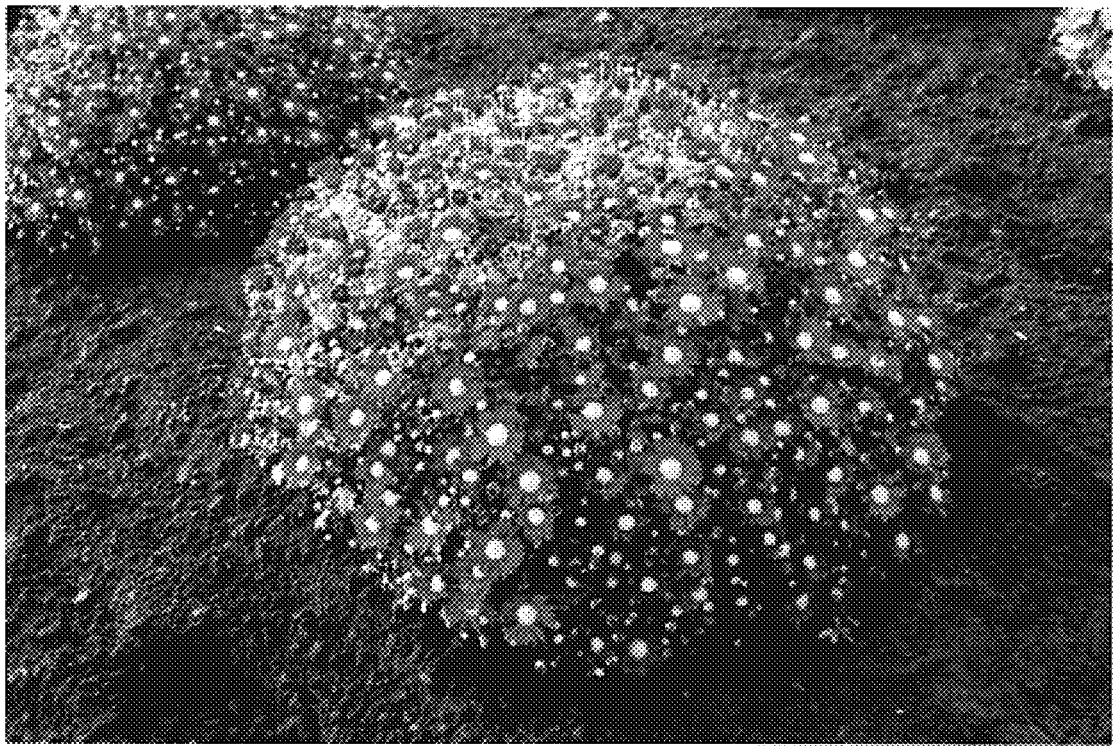
FIG. 2 is a photograph of a single plant of '00-100-216' after one year of growth.
Figure 3:
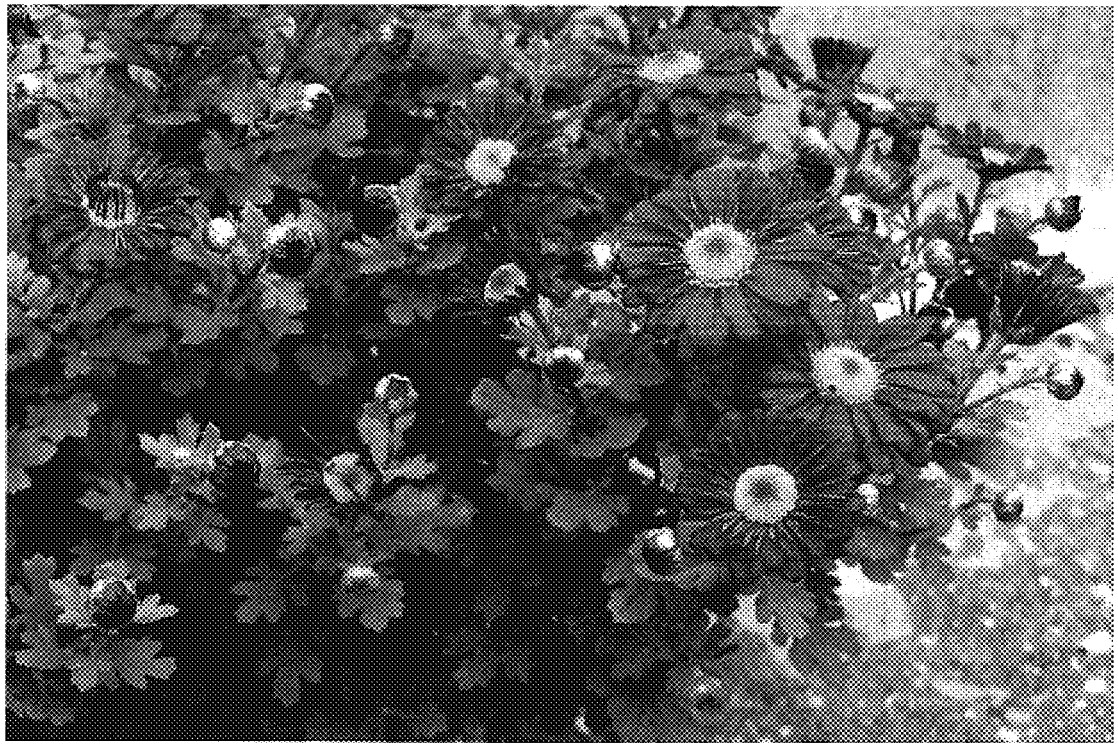

The photograph in FIG. 3 provides a close-up view of the flowers of '00-100-216'.

The colors in the photographs are as close as possible with the photographic and printing technology utilized. The color values cited in the detailed botanical description accurately describe the colors of the new *chrysanthemum*.

DETAILED BOTANICAL DESCRIPTION

The following is a description of plants the new cultivar as observed over 3 years on field grown plants in Waseca. The detailed botanical data was taken in October from one-year old plants grown outdoors in St. Paul, Minn. under natural lighting in 8-inch azalea pots produced from three cuttings that were pinched once in early spring. The phenotype of the new cultivar may vary with variations in environmental, climatic, and cultural conditions, as it has not been tested under all possible environmental conditions. The color determination is in accordance with the 2001 R.H.S. Colour Chart of the Royal Horticultural Society, London, England, except where general color terms of ordinary dictionary significance are used.

General Description:

*Blooming season.*—Early season after 6 weeks of short days.

*Plant habit.*—Herbaceous perennial, mounded habit, produces a cushion form in the first year of growth, attains a larger shrub-like habit in the second and subsequent years with a tight cushion plant form.

*Height and spread.*—Reaches about 27 cm in height and 43 cm in width in the first year in an 8-inch azalea pot. In field conditions, attains 37.5 cm in height and 53 cm in width in the first year and 44 cm in height and 89 cm in width in the second year of growth.

*Hardiness.*—U.S.D.A. Zone 3.

*Diseases resistance.*—No susceptibility or resistance to diseases common to *chrysanthemum* has been observed.

*Root description.*—Fibrous.

Growth and Propagation:

*Propagation.*—Stem cuttings.

*Time to root initiation.*—About 1 week.

*Crop maintenance.*—No pinching or pruning is required to achieve a tight cushion plant habit and abundant bloom.

*Growth rate.*—Vigorous.

Stem Description:

*Stem color.*—187A with pubescence of 198B.

*Stem surface.*—Pubescent.

*Lateral ranch length.*—Average of 12 cm (one year old plant).

*Lateral branch diameter.*—Average of 4 mm (one year-old plant).

*Quantity of lateral branches.*—About 36 lateral branches per plant (3 cuttings) produced per stem if apical meristem is removed (pinched).

*Internode length.*—Irregular.

Foliage Description:

*Leaf division.*—Simple.

*Leaf shape.*—Blade is ovate with narrow region extending towards base.

*Leaf base.*—Cuneate.

*Leaf apex.*—Acute to mucronate.

*Leaf margin.*—Incised (mulberry-like incisions) to average of 5 mm deep, incisions are also incised with 1 to 2 incisions 2 mm in depth.

*Internode length.*—Average of 1 cm.

*Leaf venation.*—Upper surface 144B, only base of mid-rib conspicuous, lower surface 144C.

*Leaf attachment.*—Sessile.

*Leaf attachment.*—Alternate.

*Leaf number.*—Average of 41 per lateral branch.

*Leaf surface.*—Puberulent on upper surface, pubescent on lower surface.

*Leaf color.*—Young foliage; upper surface 137A, lower surface 147B; mature foliage; upper surface blend of 144A and 138A, lower surface 138B.

*Leaf size (fully expanded).*—Average of 4 cm in length and 2.6 cm in width.

*Stipels.*—Lanceolate in shape, about 5 mm in width and 1.5 mm in length, color and surface the same as leaves.

*Fragrance of foliage.*—Fragrant if bruised.

Flower Description:

General Description:

*Inflorescence type.*—Composite, single daisy-type.

*Flowering response.*—6 weeks of short days.

*Lastingness of inflorescence.*—Temperature dependent, under normal field conditions during the fall, flowers typically last about 2 to 4 weeks, although flowering of the entire plant extends from 7 to 10 weeks.

*Fragrance.*—None.

*Quantity of inflorescences.*—About 150 flowers per plant (one year-old plant in 8 inch azalea pot).

*Inflorescence buds.*—About 1.3 mm in depth and diameter, globose in shape, color 59A with phyllaries 144A to 144B.

*Inflorescence size.*—About 1.5 cm in depth and 1.5 cm in diameter, diameter of disk about 5 cm.

*Peduncle.*—Strong, held upright to an angle of 45° to stem, texture is pubescent, first peduncle is an average of 4.5 cm in length and fourth peduncle is an average of about 5 cm in length, color is 187A with pubescence of 198B.

*Involucral bracts* (*phyllaries*).—144A to 144C in color, about 4 mm in length and 2 mm in width, puberulent in texture.

Ray Florets (pistillate):

*Number.*—Average of 66.

*Shape.*—Oblanceolate.

*Aspect.*—Primarily horizontal.

*Size.*—Average of 2 cm in length and 7 mm width.

*Petal apex.*—Retuse.

*Petal base.*—Cuneate.

*Petal margins.*—Entire.

*Petal texture.*—Glabrous and dull on upper surface, lower surface glabrous, waxy, and satiny.

*Petal color.*—Opening; upper surface 187B, lower surface 187C, fully open; upper surface 60A with vertical stripes of 59A, lower surface 60C to 60D suffused with 161B, fading; upper surface blend of 60C and 59D, lower surface 161B suffused with 60C.

Disk Florets (perfect):

*Quantity.*—Average of 250.

*Shape.*—Tubular.

*Size.*—About 6.5 mm in length and 2 mm in width when mature.

*Color.*—Immature; 14B with tip 178A, mature; 14A with tip 178A to 178C.

Reproductive Organs:

*Presence.*—Disk flowers are perfect, ray flowers are carpellate.

*Gynoecium.*—1 Pistil per disk and ray floret, style 5 mm in length and 145C in color, stigma 14A in color.

*Androecium.*—5 stamen per disk floret, fused into tube surrounding style, anther color 12A, pollen abundant and 14A in color.

*Fruit and seed.*—About 254 ovules per floret, fruit; an achene with a single seed attached to the ovary wall, seeds; lack pappus, have a compressed oval shape with pointed ends, about 2 to 5 mm in length and 1 to 2 mm in width with a ridged texture and 200D in color.

It is claimed:

1. A new and distinct variety of *chrysanthemum* plant designated '00-100-216' as described and illustrated herein.

* * * * *